United States Patent [19]

Terhune et al.

[11] Patent Number: 5,214,616
[45] Date of Patent: May 25, 1993

[54] NUCLEAR REACTOR VESSEL INSPECTION SYSTEM AND METHOD WITH REMOTE TRANSDUCER POSITIONING

[75] Inventors: James H. Terhune; Edward R. Dykes, both of San Jose, Calif.

[73] Assignee: General Electric Company, San Jose, Calif.

[21] Appl. No.: 745,295

[22] Filed: Aug. 15, 1991

[51] Int. Cl.⁵ .............................................. G01S 15/00
[52] U.S. Cl. ....................................... 367/99; 367/96; 73/634; 376/252
[58] Field of Search ...................... 367/95, 96, 99, 104; 73/634; 376/252; 901/9, 24, 44, 46; 364/474.05, 474.24

[56] References Cited

U.S. PATENT DOCUMENTS 4,196,049 4/1980 Burns et al. .......................... 376/252
4,881,177 11/1989 McClean et al. ...................... 73/634

*Primary Examiner*—Daniel T. Pihulic
*Attorney, Agent, or Firm*—John S. Beulick

[57] ABSTRACT

The inspection head component of a manipulator employed in the inspection of the interior surface of a nuclear reactor vessel is aligned to an optimum orientation when positioned at a local surface to be inspected. This alignment is carried out by generating ranging information with respect to the local surface using ranging ultrasonic transducers positioned upon the inspection head. The propagation interval of the acoustic signal emitted by these ranging transducers is timed and quantified to develop orientation error signals. Such development is carried out in conjunction with known values for the local surface being inspected and in conjunction with a sequence of data collection at the position. The inspection head is pivotally mounted upon the manipulator so as to be movable about at least two axes by inspection head positioning assemblies which may be provided, for example, as stepper-motors and associated translational movement components.

20 Claims, 5 Drawing Sheets

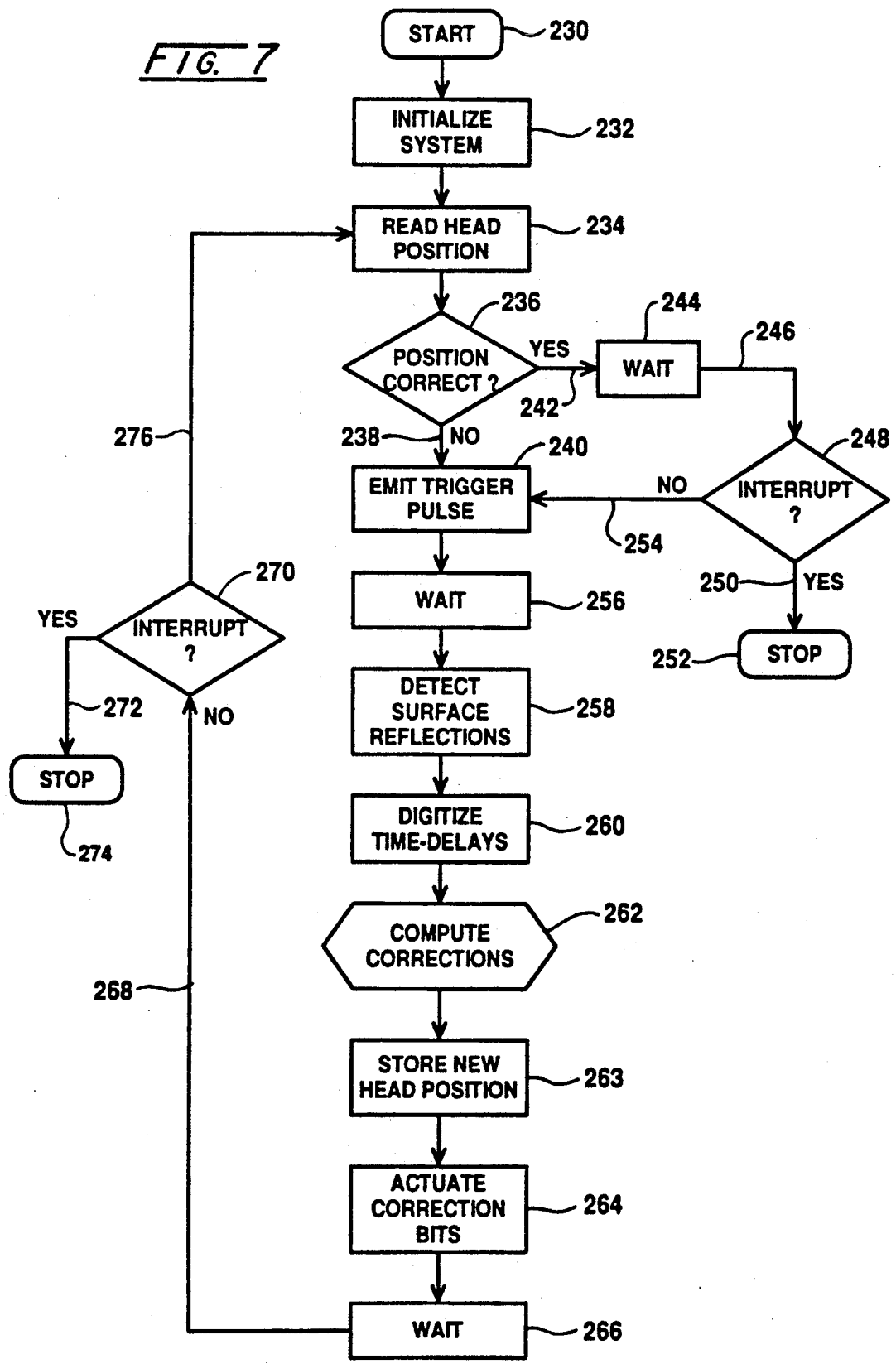

NUCLEAR REACTOR VESSEL INSPECTION SYSTEM AND METHOD WITH REMOTE TRANSDUCER POSITIONING

BACKGROUND OF THE INVENTION

Reactor vessels employed in the nuclear industry, as well as similar vessel used with large industrial facilities, in general, are fabricated as welded, curved plate structures. Typically, reactor vessels will be formed with longitudinal and circumferential seam welds, as well as nozzle welds and the like at their cylindrical or main body portions and with corresponding welds at their hemispherical top and bottom heads. Because of the criticality of maintaining the structural integrity of power reactor vessels over their somewhat extended lifespans, regulatory agencies such as the Nuclear Regulatory Commission (NRC) require extensive examination of the welds and adjacent heat affected zones within predetermined intervals. Typically, non-destructive, in-service examination and evaluation of the welded structures are carried out during scheduled shut-downs planned for such activities as refueling and the like.

Because such planned shut-downs involve a power production outage, the efficiency of their execution is most important to industries. However, the weld inspection procedure is complex, requiring control over worker radiation exposure, and thus calling for remotely controlled examination systems which themselves must be capable of operating within the environment of gamma radiation. Where boiling-water reactors (BWR) or pressurized-water reactors (PWR) are the subject of inspection, advantages have been recognized for an internal approach wherein the water media within the reactor vessel or, additionally, that within the refueling cavity, serve to isolate personnel from radiation originating from the nuclear fuel. Remotely controlled manipulators generally are employed to physically move and position inspection heads or search units carrying ultrasonic inspection transducers and/or eddy-current probes or transducers and the like to positions adjacent to the various vessel weldments and surfaces. Ultrasonic test (UT) and/or eddy-current based examinations are carried out under the control of remote stations, which may be located as far as several hundred feet from the search units mounted on the manipulator. In locating weld flaws, piezoelectric-based transducers or eddy-current probes are excited or appropriately energized by a remotely-derived signal delivered from a control system. The same or another such transducer then reacts for ultrasonic testing to a received echo or an eddy-current response is received to form an evaluating signal that is transmitted for data acquisition to the remote control station.

To achieve continuously reliable examination data during the inspection, it is important that the inspection heads carrying the transducer be properly oriented. In this regard, the transducer should retain a consistent or pre-planned orientation with respect to the curved surfaces of the inner wall of the vessel under inspection. These surfaces of interest may be planar, cylindrical, conical, spherical, parabolic or hyperbolic in nature, including, for example, nozzles. Each such geometry results in a specific pattern of response with respect to the transducer being employed and the general type of surface being inspected is typically known in advance and may be cataloged in computer memory so that digital treatment of received data can be optimized. For ultrasonic (UT) inspection procedures, pulse-echo and "pitch-catch" transducer configurations are employed in the nuclear power field. In the case of the pulse-echo configuration, the transducer, preferably, is oriented along a local normal to the small, local surface under immediate evaluation, or stated otherwise, its forward axis is oriented perpendicularly to the local tangent of the curved surface. For ultrasonic testing of the pulse-echo variety, this orientation assures an appropriate angle of incidence for an inspecting pulse and subsequently refractively affected return or echo signal. Orientation of the inspection head plane also is important with respect to pitch-catch transducer assemblies wherein two transducers are oriented for transmission and reception. Where eddy-current probes are employed, proper "altitude" or "spacing" orientation with a level surface under inspection is important. Due to the remote nature of the examination so carried out, achieving proper orientation and spacing of the transducers and their inspection heads has posed difficlties to practitioners. Typically, the manipulator controlled remote inspection heads will incorporate mechanical "feelers" or fingers which are moved into contact with the vessel interior surface to provide somewhat tactilely based orientation information. Additionally, submersible video imaging systems are employed with the manipulators to observe the interior wall and head positioning.

Present inspection head orientation approaches, however, are limited due in part to the non-uniform nature of the interior surfaces of the vessels. Generally, these walls will be covered with a stainless steel cladding having a rough outer surface. The cladding typically is formed by welding a helix of stainless steel wire to the steel wall of the vessel during its construction. Thus, surface irregularities in the form of cavities, valleys and the like are commonly encountered to disorient the inspection plane of inspection heads employing tactile positioning systems.

SUMMARY

The present invention is addressed to the system, method and apparatus for achieving an optimal orientation of an inspection head when positioned by a manipulator within a fluid adjacent to a local surface to be inspected. Having a particular application to the inspection of the interior surfaces of boiling water reactor vessels, the orientation of the inspection head is carried out by employing a non-tactile ranging system for relatively short stand-off distances involved, typically being less than 1 cm, through the use of two or more ranging ultrasonic transducers. These ranging transducers are positioned about the periphery of the inspection head. When discretely energized, they generate an acoustic output through the fluid coupling which will be present, for example, as the moderating water contained in a reactor vessel. The output impinges upon the adjacent local surfaces and reflects as an acoustic return over a propagation interval to provide an output signal. The propagation interval is timed or quantified and its value is compared with optimal orientation values to evolve orientation error signals. Maneuvering of the inspection head is carried out by mounting it in a manner wherein it is pivotal about at least two axes, for example, using a gimbal connective technique. Actuator assemblies are provided which are controlled with respect to the orientation error signals to orient the inspection head to an optimum alignment of the head axis of the inspection head with respect to the local surface under investigation. The actuating assemblies may be provided, for example, as stepper-motors or DC servo motors combined with appropriate translational mechanisms mounted between the manipulator and the inspection head.

Propagation interval timing is carried out through the utilization of the pulse sequence of a relatively high-frequency system clock in conjunction with counter components. By initiating the counting of clock pulses from the system clock at the instant of energizing the ranging transducers and terminating such counting in conjunction with the receipt of a return signal at the termination of acoustic propagation, a count may be evolved representing a numeric range value corresponding with the propagation interval. That value then is utilized in conjunction with the noted optimal orientation values to develop orientation error signals for carrying out the alignment of the inspection head.

Other objects of the invention will, in part, be obvious and will, in part, appear hereinafter.

The invention, accordingly, comprises the system, method, and apparatus possessing the construction, combination of elements, and arrangement of parts and steps which are exemplified in the following description.

For a fuller understanding of the nature and objects of the invention, reference should be had to the following detailed description taken in connection with the accompanying drawings.

BRIEF DESCRIPTION OF THE DRAWINGS

FIG. 7 is a flow chart describing a control procedure employed with the system of the invention.

DETAILED DESCRIPTION OF THE INVENTION

Figure 1:
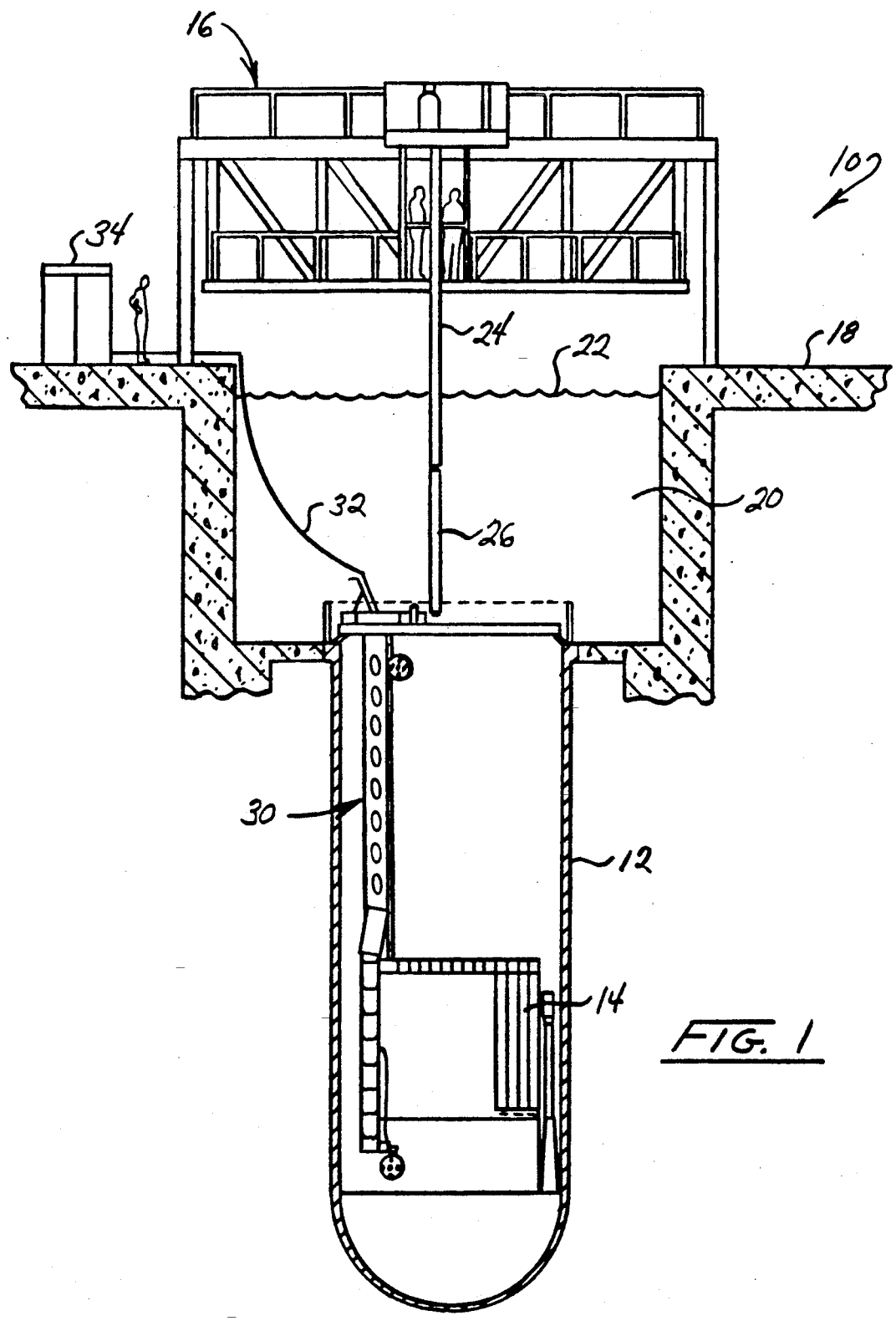
FIG. 1 is a perspective view of a nuclear facility showing refueling and interior surface inspection activities during a planned shut-down.

During planned or scheduled shut-downs of nuclear power facilities, activities such as refueling and the like are undertaken. During these activities, the collateral activities of weld seam inspection and the like may be carried out. Preferably, this inspection is performed internally such that the water contained within the reactor vessel forms a shield serving to minimize radiation exposure to personnel. Looking to FIG. 1, an example of the boiling water reactor (BWR) component of a nuclear power facility is represented schematically at 10. The facility 10 is seen to include a reactor vessel 12, the core of which at 14 is undergoing a refueling procedure during a planned shut-down. In this regard, the top head or cap of the vessel 12 is removed and refueling access to the core is provided from a refueling bridge 16. Refueling bridge 16 is seen mounted at the refueling floor 18 of the facility 10 and extends over an upper, water-filled pool or refueling cavity 20. The water level within cavity 20 is shown at 22. The refueling activity is represented by a refueling manipulator 24 shown in the process of maneuvering a fuel assembly 26. Simultaneously with this refueling procedure, a weld seam inspection manipulator assembly, represented generally at 30, is seen to be in operation and under the control of control stations and the like. These control and data acquisition stations are located remotely from the vessel 12, for example up to 200 m from vessel 12. In this regard, a flexible control and communications cable 32 is seen extending from the manipulator 30 to sub-station cabinetry 34.

Figure 2:
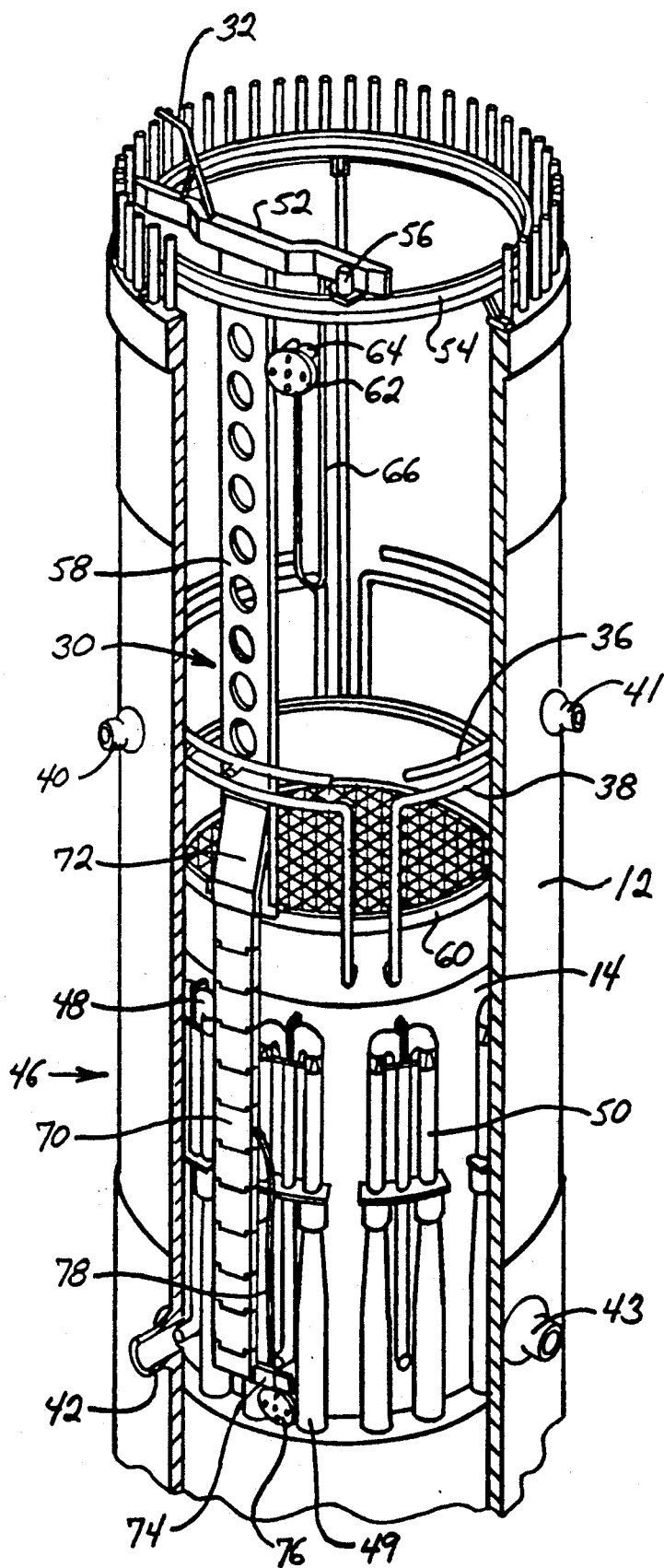
FIG. 2 is a partial sectional view of a reactor vessel and inspection manipulator mechanism with portions broken away to reveal internal structure.

Looking to FIG. 2, the reactor vessel 12 is represented at a higher level of detail, particularly showing the structuring of manipulator assembly 30. In the figure, the core again is represented at 14 and situated above the core are components typically encountered within such vessels 12, such as spargers 36 and 38, as well as a variety of nozzles as at 40-43. The core 14 is located at the belt-line region 46 of the vessel 12 and, also located at this general region, within a downcomer annulus are a sequence of elongated vertically oriented jet pumps as at 48-50. As is apparent, any manipulator such as at 30 must be configured to maneuver about these various components within the vessel 12 and to properly orient an inspection transducer such as an eddy-current device or an ultrasonic inspection component. In particular, the orientation of these components with respect to the interior surface of the vessel 12 is of importance.

Manipulator 30 is configured having an upwardly disposed circumferential car 52 which partially spans and is moved about an upper guide ring 54, for example, by a position controlling motor 56. Supported from the circumferential car 52 is a vertically oriented mast 58 which extends to and is additionally movably supported upon a lower guide ring 60. Guide rings 54 and 60 are installed by inspection personnel in the course of preparing the vessel 12 for seam weld examination procedures. Vertically movable along the elongated edge of mast 58 is an upper search unit or head 62 upon which are mounted one or more piezoelectric based ultrasonic testing transducers centrally thereof, as well as focused or unfocused piezoelectric transducers at the periphery thereof which are employed in accordance with the invention as ranging devices for orienting the axis of head 62 with respect to the interior surface of the vessel 12. Proper inspection procedure requires, for example, that the head orient the inspecting transducer such that its axis is perpendicular to any given local tangent of the interior surface of the wall or vessel 12. The search unit 62 is manipulated by a vertical travel mechanism 64 and is in control and communication connection through a shielded cable 66 with control circuitry. That circuitry, for example, may be mounted upon the mast 58, in circumferential car 52 or external to the vessel. From that circuitry, communication is further made via cabling as at 32 in the remote control and data acquisition facilities on refueling floor 18. Manipulator 30 further is capable of maneuvering an inspection assembly within the belt-line region 46 of vessel 12 through the utilization of a linked belt 70 which is coupled to the lower portion of mast 58 through a swivel guide 72. Attached to one edge of the linked belt 70 is a horizontal travel mechanism 74 which, in turn, supports a lower search unit or head 76 which is structured in the same manner as search unit 62. The horizontal travel mechanism is capable of moving vertically along one edge of the linked belt 70 and is further capable of maneuvering the search unit 76 horizontally. As in the case of search unit 62, the unit 76 incorporates not only a testing ultrasonic or eddy-current based device positioned, for example, centrally therein but also ranging ultrasonic transducers functioning to orient the head component such that the head axis representing the orientation of the testing transducer is perpendicular to a local tangent or parallel with a local normal of the interior surface of the wall of vessel 12. Through the utilization, for example of water jets, the linked belt assembly can be manipulated horizontally with respect to the interior surface of the wall. Communication between search units 76 and local control circuitry is by shielded cable such as coaxial cable 78.

Figure 3:
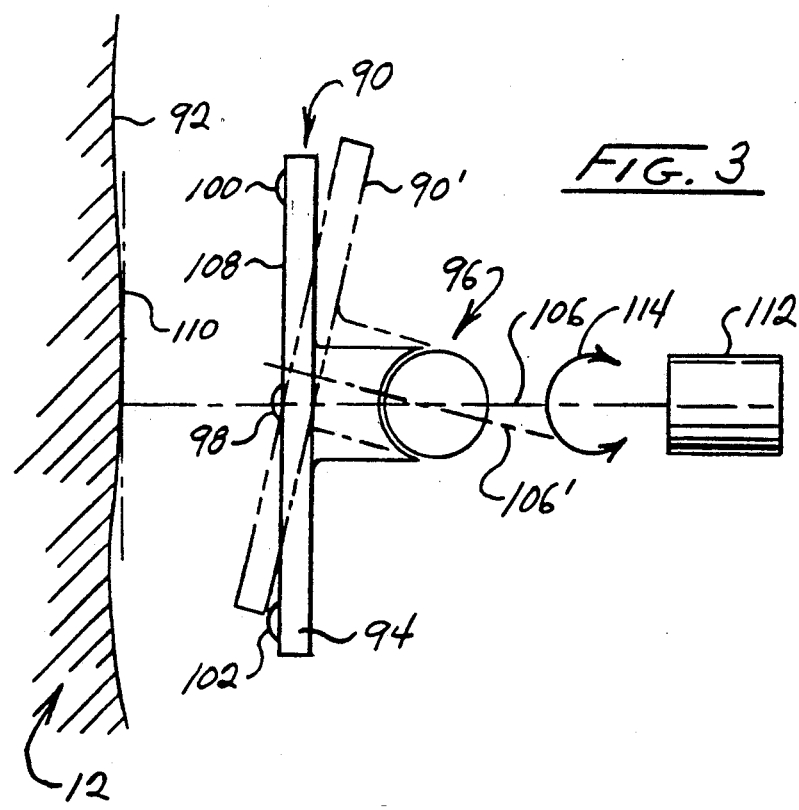
FIG. 3 is a partial side elevational view of an inspection head and adjacent local surface to be inspected with relative spacing being exaggerated in the interest of clarity.

Looking to FIG. 3, an inspection head such as may be employed at 62 and 76 is represented in simplified and exaggerated scale fashion at 90. The head 90 is shown spaced from an irregular internal surface 92 of vessel 12. That spacing, typically, will be about 1 cm. Not seen in the figure is the water couplant within the vessel 12. Head 90 includes a disk shaped head support or housing 94 which, in turn, is mounted upon, for example, mast 58 or linked belt 70 through appropriate support mechanisms which permit multi-axis gimbal movement as represented by the gimbal mounting 96. Looking additionally to FIG. 4, the housing 94 is seen to support a centrally disposed inspection transducer 98 which, for example, may be of an ultrasonic or eddy-current variety. Additionally, other such transducers may be mounted upon the housing 94. Disposed peripherally about the housing 94 are four ranging or focused ultrasonic transducers 100–103. Looking particularly to FIG. 3, a head axis 106 is shown extending centrally through the transducer 98 and orthogonally with respect to the inwardly disposed surface 108 of housing 94. Head axis 106 will having a known or predetermined sound propagational relationship to the transducer 98 and is seen extending to the irregular surface 92 of vessel 12. In this regard, for the instant demonstration, head axis 106 is seen to be perpendicular to a local tangent 110 at a local region of surface 92. To carry out optimized evaluation of the surface 92, the inspecting transducer 98 preferably is oriented having a known or consistent attitude with any local component of surface 92. Where variations occur and the orientation varies significantly, then the data evolved from the inspecting transducer 98 may be inaccurate. Such a non-standard orientation of the inspection head 90 is represented in phantom, for example, at 90', the head axis for such orientation being represented at 106'. By compiling data representing the range between the surface 92 and each of the ranging transducers 100–103, a computer controlled consistency may be evolved in the traversing activities of inspection heads as shown in the figures at 62 and 76. Since the sensitive zones of the transducers 100–103, upon their excitation, form sonic cones, in interpreting surface 92, the time-of-flight or propagation interval can be used to measure the distance to the closest point on the surface within the sonic cone or the data can be used to actively average small areas of the surface roughness, automatically measuring the mean surface orientation, or normal vector, with respect to the ranging transducer. A small manipulating device is represented in FIG. 3 at 112 in alignment with head axis 106. The device 112 may be a small position responsive motor such as a stepper-motor which functions to rotate inspection head 90 about head axis 106 as represented by the directional arrow 114.

Figure 4:
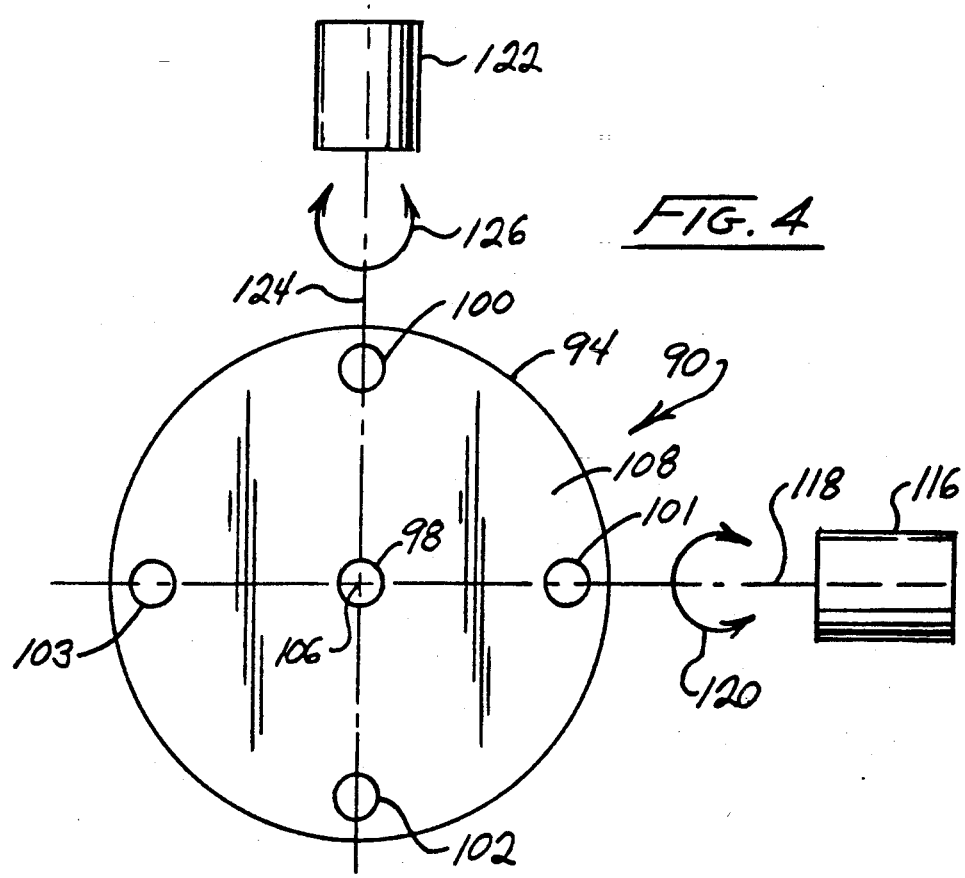
FIG. 4 is a front view of the inspection head of FIG. 3 schematically showing positioning assemblies for two axes in schematic form.

Looking to FIG. 4, a similar manipulating arrangement is provided. In this regard, a manipulating device 116 is shown aligned with transverse axis 118. Through the employment of an appropriate translational mechanism in conjunction with, for example, a stepper-motor for device 116, a rotation of the head 90 about axis 118 may be provided. In similar fashion, a manipulative device 122 such as a stepper-motor and associated translational mechanism may be employed to rotate the inspection head 90 about axis 124 as represented by the arrow 126. With the arrangement shown, head 90 may be maneuvered beneath the water surface within vessel 12 essentially with any degree of freedom desired. As noted earlier, inward and outward movement may be supplied from the manipulator assembly 30 itself.

The number of positioning assemblies as at 112, 116, and 122 required will include at least those shown at 116 and 122 for carrying out the relative adjustment of head 90 in terms of its orientation with respect to surface 92. The number of ranging devices 100–103 also may be varied to suit the needs of the user. Three and preferably four of the devices are employed for the instant orientation purpose, it being apparent that the more such devices being utilized, the more data being available for orientation analysis.

Each of the ranging transducers 100–103 is operated with a separate control. That control then provides numeric range data to a computer based control function. Looking to FIG. 5, one such control or signal generating circuit is shown generally at 130. The circuit 130 performs in conjunction with an ultrasonic transducer as represented at 132. Transducer 132 is actuated or fired by a ranging input trigger signal asserted thereto as represented at line 134 from a trigger pulse generator network represented at block 136. The network 136 will provide a triggering output pulse at line 134 having an inter-pulse interval of value greater than the maximum propagation interval anticipated for an acoustic signal to be propagated from the transducer 132 and to be reflected from the surface as at 92 back to the transducer. In this regard, the type of transducer 136 employed is of a pulse-echo variety, however, a pitchcatch method may also be used. This transmission of the signal is represented symbolically at 138. The network 136 may operate independently of any computer based system pulse or may be synchronized with a computer based clock. However, with the assertion of a ranging input trigger signal, an acoustic output which is impingeable upon the local surface 92 (FIG. 3) is generated and, simultaneously, a reset signal is provided as represented at line 140 to a binary counter 142. The ranging input trigger signal at line 134 also is directed as represented by line 144, to the reset input terminal of a reset flip-flop or monostable multivibrator 146. This resetting procedure applies a predetermined logic level such as a logic high level at the Q terminal output thereof which, in turn, is coupled by line 148 to one input of an AND gate 150. The opposite input to gate 150 is developed from a system clock represented symbolically at 152 and shown providing outputs at line 154 and 156 to the opposite input to gate 150. Line 154 also is shown being directed to the enable input of device 146. With the arrangement as shown, with the application of the reset input to device 146 from line 144 the transmission of a clock output pulse sequence to the clock input of counter 142 through line 158 may occur. In effect, device 146 in conjunction with gate 150, form a counter control network generally represented at 160 which provides a count enable function. Generally, the system clock 152 will provide a relatively high frequency pulse sequence output, for example, in the 60 to 80 MHz range.

As the acoustic signal propagated by the transducer 132 impinges upon local surface 92, it is reflected and that reflected signal will exhibit a peak amplitude characteristic as represented at wave symbol 162. Transducer 132 detects this signal and transmits a corresponding electrical signal as represented at line 164 to a peak detector 166. Detector 166 responds to the receipt of the peak amplitude to derive a detect output at line 168 which is directed to the enable input of a data latch 170. The D terminal input of latch 170 is coupled to +v source and, thus, the Q terminal output thereof at line 172 provides a logic high value representing a propagation interval termination output. Line 172 is seen to be coupled to the S terminal of RS flip-flop 146. This input, in turn, removes the logic high at the Q terminal thereof and line 148. Inasmuch as the enable input of device 146 is coupled to system clock output line 154, the presence of clock pulses from line 156 does not create an ANDing condition and the application of the sequence of pulses at line 158 is terminated. A pulse count value then is present within counter 142 which is a binary range value presented to a control computer as represented by line 174 and the symbol "$N_2$". Note that +v source is shown asserted to counter 142 to maintain its enablement throughout the operation of the signal treatment circuit represented by FIG. 5.

Figure 5:
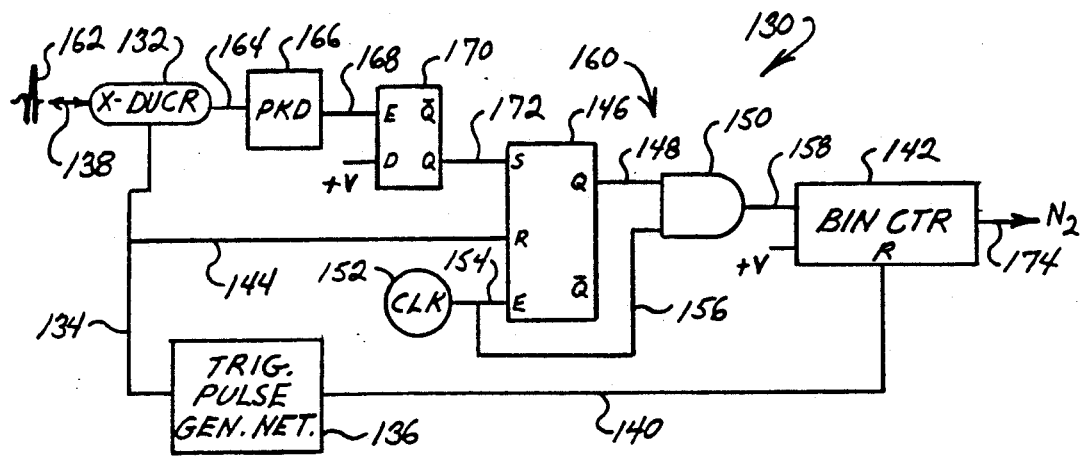
FIG. 5 is a block schematic electrical diagram showing one channel of the control system for a ranging ultrasonic transducer employed with the invention.
Figure 6:
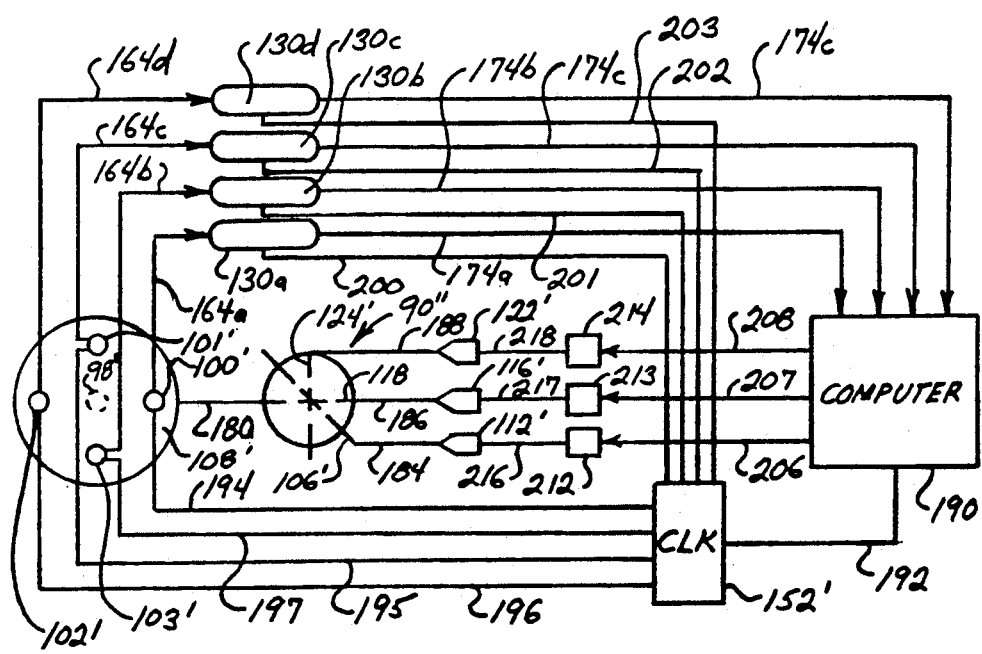
FIG. 6 is a schematic drawing of a control system for an inspection head configured according to the invention.

Referring to FIG. 6, four signal generating networks as described at 130 in connection with FIG. 5 are represented at symbols 130a-130d. Each of the networks 130a-130d is seen coupled through respective lines 164a-164d to earlier-described ranging transducer 100-103. As described in connection with FIG. 5, these lines carry the return signals from the ranging transducers. Transducers 100-103, are shown at the surface 108, now represented in dotted fashion at 108' which is associated with the housing or head 90 as shown herein at 90", the association being represented by line 180. Manipulating devices 112, 116, and 122 again are represented in the figure as stepper-motors and in primed fashion. The translational outputs of these motors are represented, respectively, at lines 184, 186, and 188. Note in this regard that line 184 is coupled with earlier-described and now primed axis 106', while line 186 is shown operatively associated with axis 118 here shown in primed fashion and line 188 is shown associated with axis 124, here also shown in primed fashion.

The controlling computer as represented at block 190 is seen to be functionally associated with clock 152, here shown in primed fashion, by an association line 192. For the instant association, the clock function 152' is synchronized with the development of the earlier-described ranging input signals or trigger signals and the trigger outputs of the clock function 152' are represented at lines 194-197 extending, respectively, to transducers 100'-103'. The high frequency system clock outputs from clock function 152' are seen directed to signal generating networks 130a-130d, respectively, through lines 200-203.

With the arrangement shown, transducers 100'-103' are triggered from respective lines 194-197 to propagate an acoustic signal to the local interior wall surface. The return echo is detected by the transducers 100'-103' and when detected, appropriate return signals are provided at respective lines 164a-164d which, in turn, are directed to signal generating circuits 130a-130d. The latter circuits generate binary values representing numeric range values at respective lines 174a-174d which are directed to the computer function 190. Computer 190 utilizes these values in conjunction with corresponding predetermined optimal orientation values to derive orientation error signals. These signals then are employed for the purpose of selectively actuating the stepper-motors 112', 116', and 122'. In this regard, the signals will be generated as binary values and presented at output lines 206-208 which, in turn, are directed to the inputs of respective digital-to-analog converters 212-214. Converters 212-214 convert the binary error signals to analog equivalent signals. These analog signals are directed as represented by lines 216-218 to stepper-motors 112', 116', and 122'. Those motors are then correspondingly energized to provide a translational correction to the head 90". There thus is developed through earlier-described respective linkages or outputs 184, 186 and 188 an optimal orientation of the head 90" with respect to head axis 106'.

Now looking to FIG. 7, a logic diagram under which the computer function 190 may perform is portrayed. The logic diagram commences with a start node 230 whereupon, as represented at block 232, the system is initialized. Following such initialization, as represented at block 234, the position of head 90 is read as it last existed in memory. With that data recalled, then, as represented at decision block 236, a determination is made as to whether the position as it exists is correct. For an initial cycle, the determination will be in the negative as represented at block 238, but with the development of data as to correct orientation, the head 90 will assume an optimal alignment. Thus, where such alignment is not achieved, a trigger pulse or ranging input signal is generated as represented at block 240. The computational cycle involved in short compared to the resultant mechanical movements of head 90 such that such movement will appear as continuous. It is smoothed by using greater than eight data bits, which also reduces quantization error.

Returning to decision block 236, where a position orientation is determined to be correct, then as represented at line 242 and block 244, a dwell or "wait" interval occurs such that the remotely located operating personnel may determine whether or not to stop the orientation program after concluding surface testing. Accordingly, the program continues as represented at line 246 and decision block 248 wherein a determination is made as to whether an interrupt from the operator has occurred. In the event that it has, then as represented at line 250 and node 252, the program stops until another start-up condition occurs. Where no interrupt is received, the program continues as represented at line 254 and block 240, the latter, as before, calling for the emission of a trigger pulse or ranging input signal. Following the emission of such signal for a given channel associated with one of the ranging transducers, as set forth at block 256, the system waits until an acoustic return occurs at the termination of a propagation interval. This waiting period represented at block 256 is selected as the maximum which the system will permit. Then, as represented at block 258, a surface reflection or acoustic return is detected. This will have been treated by the signal treatment network of FIG. 5 and will be recognized by the computer with the output at line 174. The program then continues as represented at block 260 where the time delays represented by a propagation interval are digitized. In this regard, while the output of counter 142 may be binary, some interface formatting may be called for prior to its use by the computer. Then, as represented at block 262, the program responds to the numeric range value and to a predetermined optimal orientation value to derive orientation error signals or corrections. Such corrections then develop new binary head position values which are stored as represented at block 263. Additionally, upon developing these orientation error signals, as represented at block 264, orientation error signals or correction bits are developed for selectively actuating head positioning assemblies with drives such as stepper-devices 116 and 122. Following this actuation, as represented at block 266, a wait or dwell interval occurs, again giving the operator an opportunity to interrupt the program. In this regard, the program is seen to loop as represented at line 268 to the inquiry at line 270. At this juncture, the program permits an interrupt or response to an interrupt on the part of operating personnel. Accordingly, if such interrupt is present, then as represented at line 272 and node 274, the program is stopped until the operator determines to commence it again at node 230. In the event that no interrupt is present at this point in the program, then as represented at line 276, the head 90 positions are read again from memory as represented at block 234.

Since certain changes may be made in the above system, apparatus, and method without departing from the scope of the invention herein involved, it is intended that all matter contained in the above description or shown in the accompanying drawings shall be interpreted as illustrative and not in a limiting sense.

We claim:

1. A positioning system for an inspection head carrying an inspection transducer and having a head axis and movable with a manipulator maneuverable under control within a fluid couplant to an inspection position adjacent a local surface of a body being inspected, comprising:

an actuator assembly selectively actuable for moving said head upon said manipulator to selectively align said head axis with respect to said local surface;

first and second ranging ultrasonic transducers mounted upon said inspection head, having orientations predetermined with respect to said head axis, energizable in response to a ranging input signal to generate an acoustic output impingeable upon said local surface and responsive to an acoustic return at the termination of a propagation interval to derive a return signal;

control means for deriving said ranging input signal, responsive to said return signal to derive a numeric range value representing said propagation interval, responsive to said numeric range value and a predetermined optimal orientation value to derive orientation error signals, and for actuating said actuator assembly in correspondence with said orientation error signals to effect an optimal alignment of said head axis with respect to said local surface.

2. A positioning system for an inspection head carrying an inspection transducer and having a head axis and movable with a manipulator maneuverable under control within a fluid couplant to an inspection position adjacent a local surface of a body being inspected, comprising:

an actuator assembly selectively actuable for moving said head upon said manipulator to selectively align said head axis with respect to said local surface;

first and second ranging ultrasonic transducers mounted upon said inspection head, having orientations predetermined with respect to said head axis, energizable in response to a ranging input signal to generate an acoustic output impingeable upon said local surface and responsive to an acoustic return at the termination of a propagation interval to derive a return signal; and control means for actuating said actuator assembly in correspondence with orientation error signals to effect an optimal alignment of said head axis with respect to said local surface including a system clock having a clock output pulse sequence of predetermined clock frequency, a signal generating network including: a trigger pulse generator network deriving said ranging input signal for application to said ranging ultrasonic transducers, a detector network responsive to said return signal to provide a propagation interval termination output, counter means responsive to said ranging input signal and said clock output pulse sequence to commence the counting thereof, and responsive to said propagation interval termination output to terminate said counting of said clock output pulse sequence to derive a numeric range value representing said propagation interval, said control means responsive to said numeric range value and a predetermined optimal orientation value to derive said orientation error signals.

3. The positioning system of claim 2 in which said trigger pulse generator network derives said ranging input signal as a pulse having an inter-pulse interval of length selected greater than said propagation interval.

4. The positioning system of claim 2 in which said detector network includes:

a peak detector network responsive to said return signal for deriving a detect output; and latch means, responsive to said detect output for deriving said propagation interval termination output.

5. The positioning system of claim 2 in which said counter means comprises:

a binary counter having a clock input, a reset input and an output for providing said numeric range value; and a counter control network having a first input responsive to said ranging input signal for deriving a count enable output, and to said clock output for applying said clock output pulse sequence to said binary counter clock input in the presence of said count enable output.

6. The positioning system of claim 5 in which said counter control network is responsive to said propagation interval termination output for terminating said count enable output to terminate said application of said clock output pulse sequence.

7. The positioning system of claim 5 in which said counter reset input is coupled with said trigger pulse generator network and is responsive to said ranging input signal for resetting to an initial state for commencing the generation of a said numeric range value.

8. The positioning system of claim 1 in which said actuator assembly comprises:
first stepper-motor means responsive to said range error signals having a translational output coupled with said manipulator for pivotally moving it about a first axis orthogonally disposed with respect to said head axis; and
second stepper-motor means responsive to a said range error signal to have a translational output coupled with said manipulator for pivotally moving it about a second axis orthogonally disposed with respect to said first axis and said head axis.

9. The positioning system of clam 8 in which said actuator assembly further comprises third stepper-motor means responsive to a control input from said control means for effecting a select rotation of said manipulator about said head axis; and
said control means is responsive to an operator derived input to effect derivation of said control input.

10. Inspection head apparatus for supportive connection with a manipulator maneuverable under controls within a fluid couplant to carry out the inspection of a local internally disposed surface of a reactor vessel, comprising:
a head housing having a confronting surface with an outer periphery, said housing supporting an inspection transducer, and having a head axis perpendicular to said confronting surface;
mounting means mounting said head housing upon said manipulator for pivotal movement substantially about the center thereof;
at least two spaced ranging ultrasonic transducers mounted upon said head housing adjacent said periphery, energizable in response to ranging input signals to generate an acoustic output impingeable upon said local surface and responsive to acoustic returns at the termination of propagation intervals to derive return signals;
a first head housing positioning assembly mounted between said head housing and said manipulator and actuable to pivotally move said head housing about a first axis perpendicular to said head axis;
a second head housing positioning assembly mounted between said head housing and said manipulator and actuable to pivotally move said head housing about a second axis perpendicular to said first axis and said head axis; and
control means for applying said ranging input signals to said ranging ultrasonic transducers and responsive to corresponding said return signals to derive numeric range values representing said propagation intervals, responsive to said numeric range values and memory retained optimal orientation values to derive orientation error signals, and for actuating said first and second head housing positioning assemblies in correspondence with said orientation error signals to effect an optimal alignment of said head axis with respect to said local surface.

11. The apparatus of claim 10 in which four spaced said ranging ultrasonic transducers are mounted upon said head housing adjacent to said periphery.

12. The apparatus of claim 10 including a third head housing positioning assembly mounted between said head housing and said manipulator and actuable by said control means to selectively rotate said head housing about said head axis.

13. Inspection head apparatus for supportive connection with a manipulator maneuverable under controls within a fluid couplant to carry out the inspection of a local internally disposed surface of a reactor vessel, comprising:
a head housing having a confronting surface with an outer periphery, said housing supporting an inspection transducer, and having a head axis perpendicular to said confronting surface;
mounting means mounting said head housing upon said manipulator for pivotal movement substantially about the center thereof;
at least two spaced ranging ultrasonic transducers mounted upon said head housing adjacent said periphery, energizable in response to ranging input signals to generate an acoustic output impingeable upon said local surface and responsive to acoustic returns at the termination of propagation intervals to derive return signals;
a first head housing positioning assembly mounted between said head housing and said manipulator and actuable to pivotally move said head housing about a first axis perpendicular to said head axis;
a second head housing positioning assembly mounted between said head housing and said manipulator and actuable to pivotally move said head housing about a second axis perpendicular to said first axis and said head axis; and
control means for actuating said first and second head housing positioning assemblies in correspondence with orientation error signals to effect an optimal alignment of said head axis with respect to said local surface including a system clock having a clock output pulse sequence of predetermined clock frequency, a signal generating network including: a trigger pulse generator network deriving said ranging input signals for application to said ranging ultrasonic transducers, a detector network responsive to said return signals to provide propagation interval termination outputs, counter means responsive to said ranging input signal and said clock output pulse sequence to commence the counting thereof, and responsive to said propagation interval termination output to terminate said counting of said clock output pulse sequence to derive numeric range values representing said propogation interval, said control means responsive to said numeric range values and memory retained optimal orientation values to derive said orientation error signals.

14. The apparatus of claim 13 in which said detector network includes:
a peak detector network responsive to said return signal for deriving a detect output; and
latch means, responsive to said detect output for deriving said propagation interval termination output.

15. The apparatus of claim 13 in which said counter means comprises:
a binary counter having a clock input, a reset input and an output for providing said numeric range value; and
a counter control network having a first input responsive to said ranging input signal for deriving a count enable output, and to said clock output for applying said clock output pulse sequence to said binary counter clock input in the presence of said count enable output.

16. The apparatus of claim 15 in which said counter control network is responsive to said propagation interval termination output for terminating said count enable output to terminate said application of said clock output pulse sequence.

17. The apparatus of claim 13 in which said counter reset input is coupled with said trigger pulse generator network and is responsive to said ranging input signal for resetting to an initial state for commencing the generation of a said numeric range value.

18. The method for orienting an inspection transducer mounted upon an inspection head having a head axis, and which is carried upon and movable with a manipulator within a fluid to an inspection position adjacent a local surface of a body being inspected, comprising the steps of:

providing first and second ranging ultrasonic transducers mounted in mutually spaced relationship about the periphery of said inspection head and energizable to generate an acoustic output impingeable upon said local surface and responsive to an acoustic return at the termination of a propagation interval to derive a return signal;

mounting said inspection head for pivotal movement about a first axis perpendicular to said head axis and about a second axis perpendicular to said first axis and said head axis;

providing a first inspection head positioning assembly mounted between said inspection head and said manipulator and actuable to pivotally move said inspection head about said first axis;

providing a second inspection head positioning assembly mounted between said inspection head and said manipulator and actuable to pivotally move said inspection head about said second axis;

moving said inspection head with said manipulator to said inspection position adjacent said local surface;

energizing said first ranging transducer;

timing the propagation interval of said energized first ranging transducer and deriving a first numeric range value therefrom;

energizing said second ranging transducer;

timing the propagation interval of said energized second ranging transducer and deriving a second numeric range value therefrom;

comparing said first and second numeric range values with corresponding optimal orientation values and deriving first and second orientation error signals;

actuating said first and second inspection head positioning assemblies in correspondence with said first and second orientation error signals to effect a predetermined alignment of said head axis with respect to said local surface.

19. The method of claim 18 including the steps of:

providing third and fourth ranging ultrasonic transducers mounted in spaced relationship with said first and second ranging ultrasonic transducers about the periphery of said inspection head and energizable to generate an acoustic output impingeable upon said local surface and responsive to an acoustic return at the termination of a propagation interval to derive a return signal;

energizing said third and fourth ranging ultrasonic transducers;

timing the propagation intervals of said energized third and fourth ranging transducers and deriving respective third and fourth numeric range values therefrom;

comparing said third and fourth numeric range values with corresponding optimal orientation values; and deriving said first and second orientation error signals with respect to said first, second, third and fourth numeric range value comparisons.

20. The method for orienting an inspection transducer mounted upon an inspection head having a head axis, and which is carried upon and movable with a manipulator within a fluid to an inspection position adjacent a local surface of a body being inspected, comprising the steps of:

providing first and second ranging ultrasonic transducers mounted in mutually spaced relationship about the periphery of said inspection head and energizable to generate an acoustic output impingeable upon said local surface and responsive to an acoustic return at the termination of a propagation interval to derive a return signal;

mounting said inspection head for pivotal movement about a first axis perpendicular to said head axis and about a second axis perpendicular to said first axis and said head axis;

providing a first inspection head positioning assembly mounted between said inspection head and said manipulator and actuable to pivotally move said inspection head about said first axis;

providing a second inspection head positioning assembly mounted between said inspection head and said manipulator and actuable to pivotally move said inspection head about said second axis;

moving said inspection head with said manipulator to said inspection position adjacent said local surface;

energizing said first ranging transducer;

timing the propagation interval of said energized first ranging transducer and deriving a first numeric range value therefrom by:

providing a system clock sequence of pulses at a predetermined fixed frequency;

providing a counter for receiving said sequence of pulses and carrying out the counting thereof between run and stop inputs;

providing said run input in response to said energization of said first ranging transducer; and providing said stop input in response to said return signal; energizing said second ranging transducer;

timing the propagation interval of said energized second ranging transducer and deriving a second numeric range value therefrom;

comparing said first and second numeric range values with corresponding optimal orientation values and deriving first and second orientation error signals; and actuating said first and second inspection head positioning assemblies in correspondence with said first and second orientation error signals to effect a predetermined alignment of said head axis with respect to said local surface.

* * * * *